(12) United States Patent
Maier et al.

(10) Patent No.: US 9,861,745 B2
(45) Date of Patent: ***Jan. 9, 2018

(54) SYSTEM AND METHOD FOR MONITORING TIME INTERVALS DURING BLOOD PARAMETER MONITORING

(75) Inventors: Hans-Otto Maier, Melsungen (DE); Torsten Doenhoff, USA River (TZ); Horst Schmoll, Guxhagen (DE); Matthias Paetzold, Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 982 days.

This patent is subject to a terminal disclaimer.

(21) Appl. No.: 13/579,858

(22) PCT Filed: Mar. 3, 2011

(86) PCT No.: PCT/EP2011/053244
§ 371 (c)(1),
(2), (4) Date: Dec. 18, 2012

(87) PCT Pub. No.: WO2011/107567
PCT Pub. Date: Sep. 9, 2011

(65) Prior Publication Data
US 2013/0085471 A1    Apr. 4, 2013

(30) Foreign Application Priority Data

Mar. 5, 2010  (DE) .................. 10 2010 010 567
Mar. 24, 2010 (DE) .................. 10 2010 012 733

(51) Int. Cl.
*A61M 5/172*  (2006.01)
*A61B 5/157*  (2006.01)
(Continued)

(52) U.S. Cl.
CPC ........... *A61M 5/1723* (2013.01); *A61B 5/157* (2013.01); *A61B 5/145* (2013.01); *A61B 5/155* (2013.01);
(Continued)

(58) Field of Classification Search
CPC .. A61M 5/142; A61M 5/168; A61M 5/16804; A61M 5/16827; A61M 5/16831;
(Continued)

(56) References Cited

U.S. PATENT DOCUMENTS

2004/0172284 A1   9/2004  Sullivan et al.
2005/0019943 A1   1/2005  Chaoui
(Continued)

FOREIGN PATENT DOCUMENTS

EP     2 186 480       5/2010
JP     2009 273 502    11/2009
(Continued)

OTHER PUBLICATIONS

International Preliminary Report on Patentability for PCT/EP2011/053244, dated Sep. 25, 2012.
(Continued)

*Primary Examiner* — Shefali Patel
(74) *Attorney, Agent, or Firm* — RatnerPrestia

(57) ABSTRACT

A system and a method for monitoring at least one blood parameter of blood of different patients, comprising a plurality of access devices for establishing at least one access to the blood of each patient through skin, a plurality of removal devices for removing a quantity of the blood from each patient in order to obtain at least one blood sample, at least one blood analysis device for analyzing the at least one blood sample with respect to predeterminable blood parameters and for generating individual blood parameter data sets, a calculation device which can be used jointly for a
(Continued)

plurality of blood parameter data sets of the different patients for calculating data sets of drug parameters of drugs to be administered to a respective patient on the basis of the individual blood parameter data sets, and a plurality of supply devices for supplying a respective drug having the calculated data sets of the drug parameters.

10 Claims, 2 Drawing Sheets

(51) Int. Cl.
| | |
|---|---|
| *A61B 5/145* | (2006.01) |
| *A61B 5/155* | (2006.01) |
| *A61B 5/00* | (2006.01) |
| *A61M 5/142* | (2006.01) |
| *G01N 27/327* | (2006.01) |
| *G01N 35/00* | (2006.01) |
| *G01F 19/00* | (2006.01) |
| *A61B 5/15* | (2006.01) |
| *G06F 19/00* | (2011.01) |

(52) U.S. Cl.
CPC ... *A61B 5/150229* (2013.01); *A61B 5/150236* (2013.01); *A61B 5/150244* (2013.01); *A61B 5/150389* (2013.01); *A61B 5/150503* (2013.01); *A61B 5/150786* (2013.01); *A61B 5/4839* (2013.01); *A61B 2562/08* (2013.01); *A61M 5/14244* (2013.01); *A61M 2005/14208* (2013.01); *A61M 2205/60* (2013.01); *A61M 2205/6009* (2013.01); *A61M 2230/201* (2013.01); *G01N 27/3271* (2013.01); *G01N 2035/00881* (2013.01); *G01N 2800/52* (2013.01); *G06F 19/3468* (2013.01)

(58) Field of Classification Search
CPC .......... A61M 5/16836; A61M 5/16877; A61M 5/172; A61M 5/1723; A61M 2005/14208; A61M 2005/1726; A61M 2205/3327; A61M 2205/60; A61M 2205/6009; A61M 2205/6063; A61M 2205/6072; A61M 2205/84; A61M 2230/20; A61B 2562/08; A61B 5/145; A61B 5/150786; A61B 5/155; A61B 5/157; A61B 5/4839
USPC ...................... 604/65, 66, 67, 500, 503, 504
See application file for complete search history.

(56) References Cited

U.S. PATENT DOCUMENTS

| | | | |
|---|---|---|---|
| 2005/0139651 A1* | 6/2005 | Lim | A61M 5/14 235/380 |
| 2005/0154368 A1 | 7/2005 | Lim et al. | |
| 2006/0009949 A1 | 1/2006 | Seher et al. | |
| 2006/0229551 A1 | 10/2006 | Martinez et al. | |
| 2008/0021436 A1* | 1/2008 | Wolpert | A61B 5/14532 604/504 |
| 2008/0306435 A1 | 12/2008 | Kamath et al. | |
| 2009/0055223 A1 | 2/2009 | Jung et al. | |
| 2009/0099438 A1 | 4/2009 | Flanders | |
| 2009/0131861 A1 | 5/2009 | Braig et al. | |
| 2010/0001876 A1 | 1/2010 | Sasaki | |
| 2010/0036310 A1 | 2/2010 | Hillman | |
| 2010/0121170 A1* | 5/2010 | Rule | A61B 5/1427 600/365 |

FOREIGN PATENT DOCUMENTS

| | | |
|---|---|---|
| RU | 2148257 | 4/2000 |
| WO | WO 2005/050497 | 6/2005 |
| WO | WO 2008/083313 | 7/2008 |
| WO | WO 2009/031636 | 3/2009 |

OTHER PUBLICATIONS

Written Opinion for Singapore SG 201206086-9 dated Nov. 15, 2013.
International Search Report for PCT/EP2011/053244, dated Jul. 15, 2011.
Australian Examination report corresponding to patent application No. 2011222943 dated Jul. 12, 2013.
Singaporean Search Report corresponding to patent application No. 201206086-9 dated Apr. 26, 2013.
Exam Report for CA 2,789,191 dated Oct. 2, 2014.
European Office Action with translation for DE 11 707 397.3 dated Jul. 29, 2013.
Translation of Decision on Grant for Russian application No. 2012134289/08 (054763) dated Nov. 13, 2014.
Translation of Mexican Office Action for MX/a/2012/009596 dated Nov. 5, 2013.
European Exam Report (with translation) for EP 11 707 397.3 dated Oct. 26, 2015.
Translation of Chinese Exam Report for CN 201180010460.7 dated Feb. 24, 2016.
Canadian Examination Report dated Sep. 27, 2016 for Canadian Application No. 2789191, 6 pages.

* cited by examiner

SYSTEM AND METHOD FOR MONITORING TIME INTERVALS DURING BLOOD PARAMETER MONITORING

CROSS-REFERENCE TO RELATED APPLICATIONS

This application is a U.S. National Stage Application under 35 U.S.C. §371 of International Application No. PCT/EP2011/053244, filed Mar. 3, 2011, which claims the benefit of German Application Nos. 10 2010 010 567.8, filed Mar. 5, 2010, and 10 2010 012 733.7, filed Mar. 24, 2010.

FIELD OF THE INVENTION

The invention concerns a system and a method for monitoring at least one blood parameter of the blood of different patients with a multiplicity of access devices each to create at least one access to the blood of each patient through his or her skin, a multiplicity of extraction devices each to extract a blood quantity from each patient to obtain in each case at least one blood specimen, at least one blood analysis device to analyse the blood specimen in relation to predefinable parameters of the blood and to generate individual blood parameter data sets, a calculation device which can be used in common for a multiplicity of blood parameter data sets of different patients to calculate data sets of medicament parameters of the medicaments to be administered to the respective patient on the basis of the individual blood parameter data sets, and a multiplicity of supply devices to supply the respective medicament with the calculated medicament parameters according to the preambles of the independent claims.

BACKGROUND OF THE INVENTION

Conventionally patients, in particular those on the intensive care ward, are supplied with medicaments and where applicable artificial nutrition by means of one or more supply devices, for example intravenously or by mean of gastric probes. For example the supply device can be an insulin supply device or an infusion pump respectively which keeps the insulin value present within the patient's blood circulation at a predefinable level in reaction to a blood glucose value of the patient's blood circulation previously measured. Also supply devices can be used for administration of at least one nutrient of a nutrition supplied to the patient directly or indirectly by means of one nutrition supply device.

Such supply devices, even when integrated in a system for administration of medicaments and/or nutrients, have previously required the input of values by a doctor or further clinical personnel to form the basis of the supply by means of a supply device. For example here quantity values, time intervals at which the supply should take place, intermittent supplies etc. can be entered as the basis for the subsequent supply of for example insulin.

Before this supply usually blood must be extracted from the patient, usually manually, which requires the intervention of clinical personnel. Also further clinical personnel are required who have the necessary specialist knowledge of the input functions of the supply device such as the infusion pump in order then to perform the supply.

Frequently this leads to the problem that incorrect procedures take place due to the intervention of clinical personnel. For example it is conceivable that a blood specimen is associated with the wrong patient and hence there is a risk of administration of incorrect medicaments both on input of data to the supply device as well as on blood extraction and also on performance of blood analysis.

In addition such supply devices such as infusion pumps have a delivery rate which is shown as a volume per time unit (ml/h). In contrast in medicine the dose unit is used for a supplied medicament solution. Consequently it is necessary to convert the dose unit into a delivery rate of the pump, which is the task of the treating doctor. The disadvantage in such a conversion is that calculation errors can frequently occur which lead to incorrect input of the delivery rate and hence an incorrect administration of insulin to the patient.

It is also conceivable that the dose unit can be entered on an infusion pump. However, this requires data to be taken into account on the concentration of active substance of the medicament to be administered and the type of medicament. Both when giving the concentration of active substance and on input of the dose unit and its conversion into the delivery rate, previously exclusively the main active substances of the medicament were taken into account. This is often sufficient insofar as only or primarily one specific medicament is to be administered.

Supply devices or delivery devices respectively for the supply of a medicament solution mixture to a body are known in many ways. For example devices or systems are known with a multiplicity of infusion and/or injection pumps, each of which each supplies one solution with at least one specific medicament active substance to a body and thus a medicament solution mixture results.

Such infusion pump systems are often used on patients requiring intensive medicinal treatment. Here the infusion pumps have the properties of continuous and precise dosing of medication in the supply. To achieve an optimised matching of the dosing of these pumps, the pumps are integrated into a common system which usually has a central control unit, an operating unit and an alarm unit.

The data connection of several pumps and/or control units can also be combined in a server. This allows, where applicable in an additional calculator unit/medicinal computer, that even a two-digit quantity of different medicaments can be matched to a body and supplied precisely dosed. The data are distributed to the different infusion pumps hardwired or by wireless LAN.

Also in the case of use of a server, the problem often occurs that correct association of the medicaments determined with the associated medicament parameters to the correct infusion pump or multiplicity of infusion pumps belonging to the patient with the determined blood parameter values, is not guaranteed due to the intervention of clinical personnel.

Also by means of the common server, a multiplicity of pumps or delivery devices respectively can be controlled which are arranged at various patients and serve to supply these various patients.

SUMMARY OF THE INVENTION

Consequently the object of the invention is to propose a system and a method for monitoring at least one blood parameter of the blood of different patients in which a fault-free association of calculated medicament parameters to the respective supply devices is ensured.

This object is achieved by the systems and methods with the features of the independent claims.

It is an essential point of the invention that in a system for monitoring at least one blood parameter of the blood of different patients with a multiplicity of access devices each to create at least one access to the blood of each patient through his or her skin, a multiplicity of extraction devices each to extract a blood quantity from each patient to obtain in each case at least one blood specimen, at least one blood analysis device to analyse the blood specimen in relation to predefined parameters of the blood and to generate individual blood parameter data sets, a calculation device which can be used in common for a multiplicity of blood parameter data sets of different patients to calculate data sets of medicament parameters of the medicaments to be administered to the respective patient on the basis of the individual blood parameter data sets, and a multiplicity of supply devices to supply the respective medicament with the calculated medicament parameters, an association device is provided to allocate in each case an identification code to identify a patient and/or a period of time code to specify a period of time in which the blood sample was taken, to each data set of the medicament parameters calculated by the calculation device of a patient. Such an association device is advantageously arranged within the calculation device.

Advantageously such an association device can be used to ensure that the blood parameter data sets obtained from the blood analysis device by the calculation device are reliably associated with the correct identification code and/or correct time section code, in order to ensure that the resulting medicament parameter data sets are sent to the correct supply device which can be an infusion pump for administration of insulin in response to a blood glucose level previously measured. In this way it is excluded that calculated medicament parameter data sets are transmitted to the wrong infusion pump and hence a patient receives an incorrect administration, such as can be the case for example on intervention of medicinal personnel for the input of data sets at the infusion pumps. The data sets of the medicament parameters may also be encrypted.

Also the association of a period of time code can ensure that on extraction of several blood specimens from the same patient, it is guaranteed that it is not previously calculated medicament parameters data sets which are sent to the infusion pump associated with the patient, but only the medicament parameter data set which was last calculated in conjunction with the identification code for the selected patient.

Advantageously each data set of medicament parameters for a patient together with the identification code and period of time code can be transmitted as a common data set by hard-wired or wireless link from the calculation device to one or more supply devices. The common data set may be in the form of binary code. Because of the wireless transmission, a physical separation is possible of the calculation device which can be arranged within a common server and the individual supply devices which are usually arranged as infusion pumps in different rooms of a hospital immediately next to the patient.

At least one identification element generating device is preferably used to ensure that each blood specimen, immediately after taking the blood quantity and before supply to the blood analysis device, the identification code and/or the period of time code in the form of a barcode, a data matrix code and/or a transponder on the extraction device is allocatable containing the blood specimen.

Advantageously a method for monitoring at least one blood parameter of the blood of different patients comprises the following steps:

Method for monitoring in each case at least one blood parameter of the blood of different patients (1, 2, 3) with the following steps;

creation in each case of at least one access to the blood of each patient (1, 2, 3) by means of a multiplicity of access devices (1a, 2a, 3a);

extraction (30) of a blood quantity from each patient (1-3) to obtain in each case at least one blood specimen, by means of a multiplicity of extraction devices (1b, 2b, 3b);

analysis (32) of the blood specimen in relation to predefinable parameters of the blood by means of a multiplicity of blood analysis devices (7, 9) which can be used for blood specimens of different patients (1-3);

calculation (35) of medicament parameters of the medicaments to be administered to the respective patients on the base of data sets of the determined parameters of the analysed blood, by means of a common calculation device (15); and supply (37) of the respective medicament with the calculated medicament parameters by means of a multiplicity of supply devices (19, 20, 21), wherein by means of an association device (13), in each case an identification code to identify a patient and/or a period of time code to specify a period of time in which in the blood extraction took place, is associated with each data set of the parameters determined by the blood analysis device (7, 9) of the analysed blood of a patient (1-3) (33).

In such a method each data set of determined parameters of the analysed blood together with the identification code and period of time code, is transmitted as a common data set wirelessly or hard-wired from the blood analysis device (7, 9) to one or more of the supply devices (19, 20, 21). Within the common data set, the data set of medicament parameters may be frequency-modulated and/or amplitude-modulated with the data of the identification code and/or the data of the period of time code.

BRIEF DESCRIPTION OF THE DRAWINGS

Further advantageous embodiments arise from the subclaims and the description below in conjunction with the drawing, wherein:

FIG. 1 diagrammatically shows the system according to the invention in one embodiment of the invention.

DETAILED DESCRIPTION OF THE PREFERRED EMBODIMENTS

Figure 1:
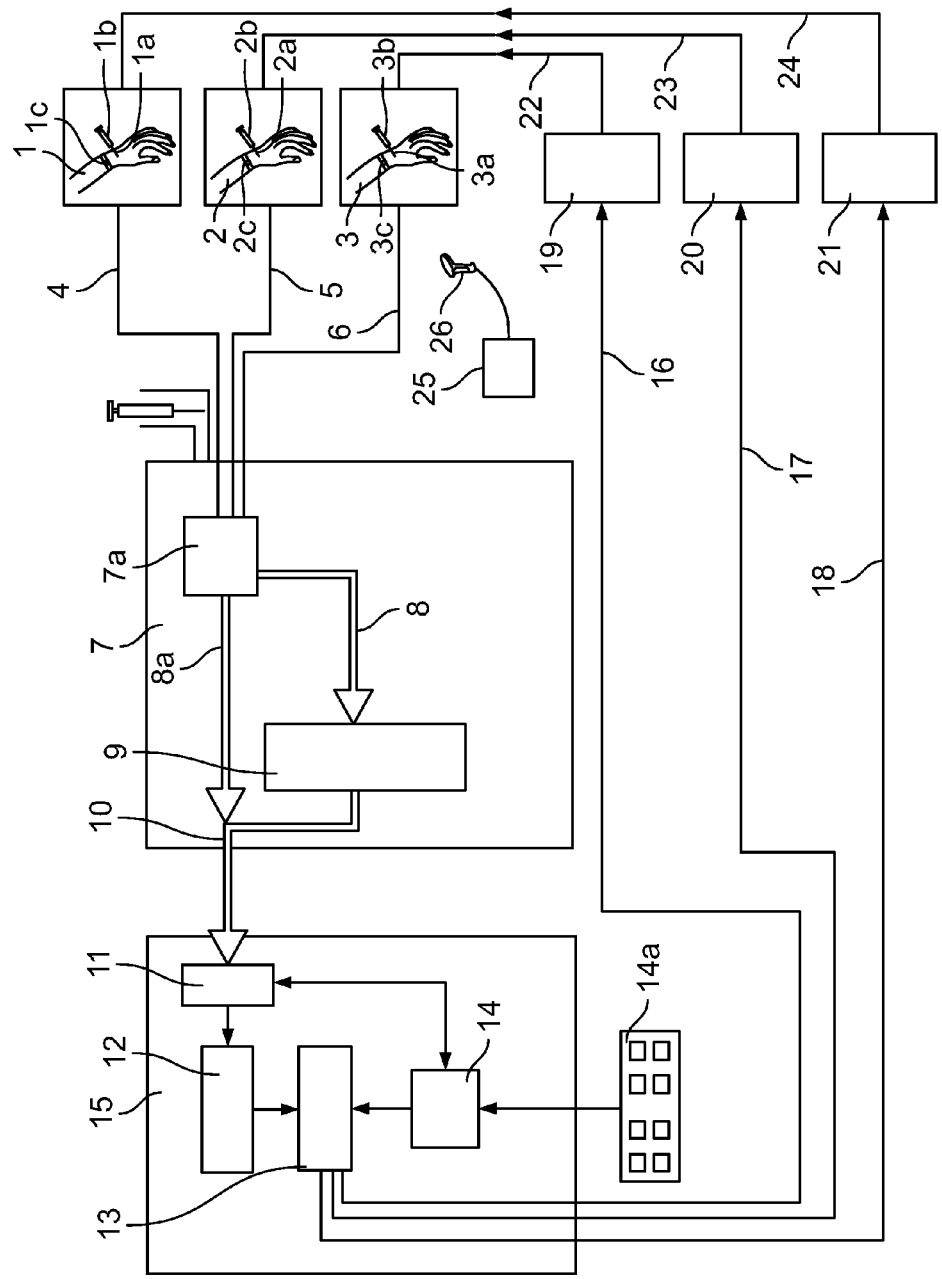
FIG. 1 diagrammatically shows the system according to the invention according to one embodiment of the invention in its function sequence, and FIG. 2 in a flow diagram shows the method according to the invention according to one embodiment of the invention.

As evident from the depiction in FIG. 1, blood is taken from a total of three hospital patients 1, 2, 3 by means of a blood extraction system (e.g. a syringe 1b, 2b, 3b which each has a needle 1a, 2a and 3a). Each patient has on his arm an armband 1c, 2c, 3c on which patient-specific data is arranged, for example by means of a barcode, a data matrix code or a transponder. These data can for example be the identification codes of the patient.

As soon as a blood specimen is taken by means of the blood extraction system 1b, 2b and 3b, these specimen containers (e.g. syringe) are transported according to the transport routes 4, 5 and 6 shown to a blood analysis device 7.

At the same time or before this, by means of a barcode or data matrix code reader 26 or a read unit for transponders, the codes on the armband 1c, 2c and 3c of the patients 1, 2, 3 are read and by means of a barcode or data matrix code generating device 25 or by means of a write unit for transponders, a corresponding barcode or data matrix code is printed out or a transponder written. This barcode or data matrix code or this transponders is glued on the outside to the respective specimen container (e.g. syringe).

On arrival at the blood analysis device 7, these barcodes, data matrix codes and/or transponders are read by means of a read unit 7a and at the same time the blood specimens entered in the blood analysis device.

A subsequent data transfer from the read unit 7 to an analysis unit 9 within the blood analysis device 7, as indicated by reference numeral 8, leads to the identification code and the period of time code being transmitted to the analysis unit and according to reference numeral 10 to an association device 13, wherein at the same time within the analysis unit 9 an analysis of the blood specimen takes place to establish predefinable blood parameters.

The blood parameter data sets produced by the analysis unit are transmitted wirelessly or hard-wired by means of a common line 10 to a receiver unit 11 of a calculation device 15. This receiver unit also receives, as shown with reference numeral 8a, data on the identification code and period of time code. Both the identification code data and the period of time code data and the blood parameter data sets are passed on by the receiver unit 11 to the calculation unit 12 which calculates from the transmitted blood parameter data sets the medicament parameter data sets which must be determined for administration of the medicaments.

Then the calculation unit 12 passes on the calculated medicament parameter data sets to an association device 13 which is able to allocate one of the transmitted identification codes and/or period of time codes to each calculated medicament parameter data set.

In addition by means of a keyboard 14a or similar input device, further parameters can be entered in a memory unit 14 or even by communication with the receiver unit 11, the correspondingly transmitted identification codes and period of time codes for the respective blood parameter data set can be modified. This is then transmitted further to the association device 13 for correct association to the calculated medicament parameter data set.

According to reference numerals 16, 17 and 18, a transmission then takes place of the common data sets which are composed of a data set of the calculated medicament parameters and an identification code and/or a period of time code to the associated supply devices 19, 20 and 21 selected on the basis of the identification code and the period of time code, which devices as infusion pumps administer as a medicament for example insulin to the respective patient 1, 2, 3, as indicated by reference numerals 22, 23 and 24.

Figure 2:
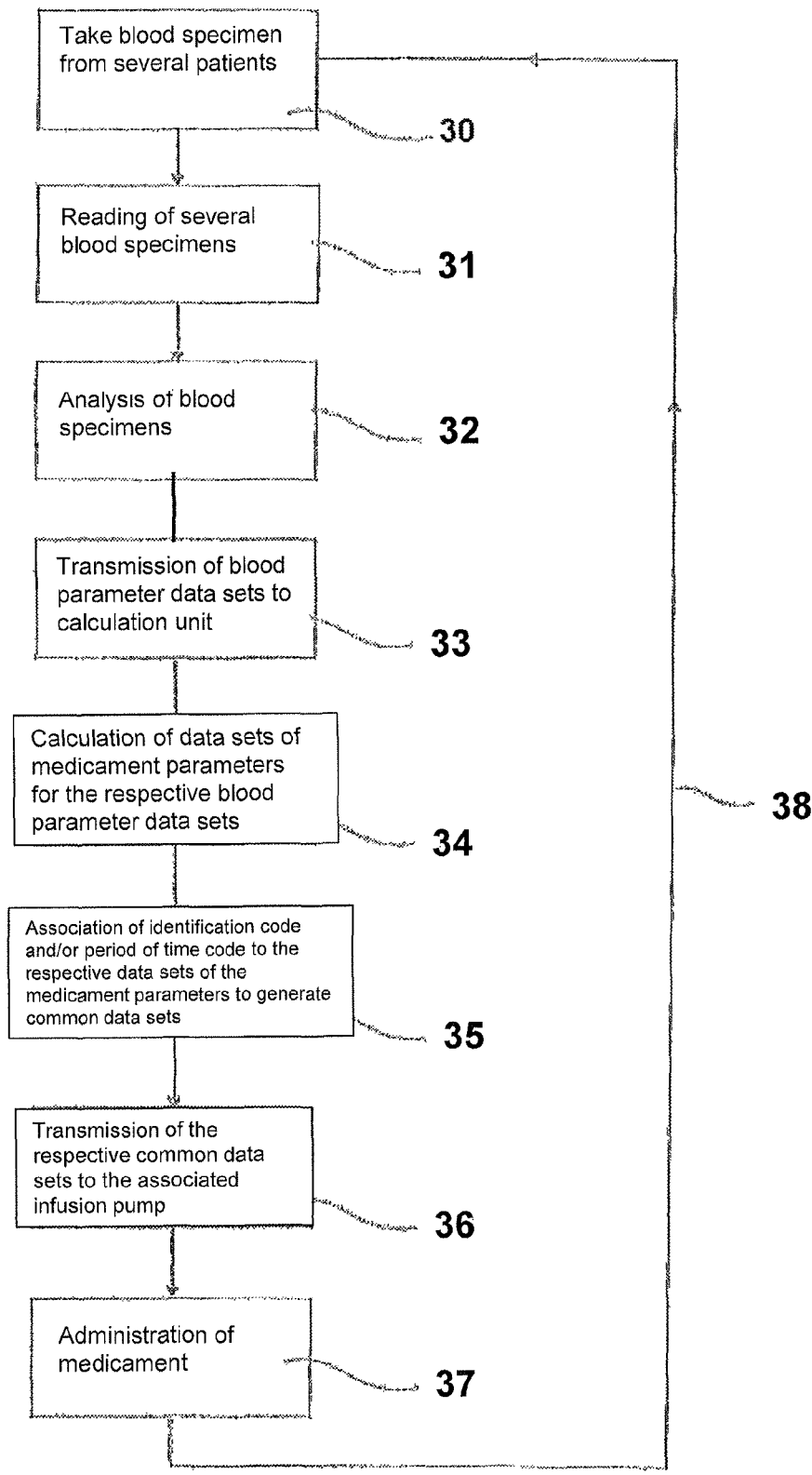

In the flow diagram according to FIG. 2, a method is shown according to one embodiment of the invention.

It is clear from this depiction that in an initial step 30 blood specimens are taken from several patients which are then read into the blood analysis device (step 31).

After analysis of the blood specimen according to step 32, in step 33 blood parameter data sets which result from the collective blood analysis are transmitted to the calculation device.

In the calculation device data sets are calculated of the medicament parameters for the respective blood parameter data sets according to step 34 in order then in step 35 to allow association of the identification code and period of time code to the respective data sets of the medicament parameters to generate common data sets.

After transmission of the common data set to the associated infusion pump according to step 36, the medicament is administered in step 37.

Reference numeral 38 shows that after a predefinable period of time a further blood sample is taken according to step 30 and hence there is a closed circuit.

Certain features disclosed in the application are understood to be novel, including for example, features either individually or in combination with other features as compared with the prior art.

LIST OF REFERENCE NUMERALS

1 Patient 1
1a Needle for patient 1
1b Syringe for patient 1
1c Armband for patient 1
2 Patient 2
2a Needle for patient 2
2b Syringe for patient 2
2c Armband for patient 2
3 Patient 3
3a Needle for patient 3
3b Syringe for patient 3
3c Armband for patient 3
4 Transport route
5 Transport route
6 Transport route
7 Blood analysis device
7a Read unit
8 Data transfer
9 Analysis unit
10 Common line
11 Receiver unit
12 Calculation unit
13 Association device
14 Memory unit
14a Keyboard
15 Calculation device
16 Transmission of medicament parameters to infusion pump
17 Transmission of medicament parameters to infusion pump
18 Transmission of medicament parameters to infusion pump
19 Supply device
20 Supply device
21 Supply device
22 Administration of correct dose of insulin
23 Administration of correct dose of insulin
24 Administration of correct dose of insulin
25 Barcode or data matrix code generating unit
26 Data matrix code reader
30 Extraction of blood quantity
31 Reading of blood specimens in the blood analysis device
32 Analysis of blood specimen
33 Transmission of blood parameter data sets
34 Calculation of medicament parameter
35 Association of codes of medicament parameters
36 Transmission of medicament parameters to infusion pumps
37 Administration of medicament
38 Method circuit

The invention claimed is:
1. A system for monitoring at least one blood parameter of blood of different patients, the system comprising:

a multiplicity of access devices each to create at least one access to the blood of each patient through his or her skin;

a multiplicity of extraction devices each to extract a blood quantity from each patient to obtain in each case at least one blood specimen;

at least one blood analysis device to analyse the at least one blood specimen in relation to predefinable parameters of the blood and to generate individual blood parameter datasets;

a calculation device which can be used in common for a multiplicity of blood parameter data sets of the different patients to calculate data sets of medicament parameters of medicaments to be administered to a respective patient on the basis of the individual blood parameter data sets;

a multiplicity of supply devices to supply the respective medicaments to the respective different patients in accordance with the calculated data sets of the medicament parameters for each of the different patients, and an association device configured to:
  allocate in each case an identification code to identify a patient and a period of time code to specify a period of time in which the at least one blood specimen was taken, to each data set of the medicament parameters calculated by the calculation device, such that a common data set is created for each respective patient; and
  transmit each common data set including a respective data set of the calculated data sets of the medicament parameters for each of the different patients together with the identification code and the period of time code, from the calculation device by a hard-wired link or a wireless link to a respective supply device, wherein each respective supply device is selected based on the identification code and the period of time code; and
each respective supply device supplies a corresponding amount of a respective medicament according to the common data set for each respective patient.

2. The system according to claim 1, wherein the association device is arranged in the calculation device.

3. The system according to claim 1, further comprising at least one identification element generating device, by means of which, immediately after taking of the blood quantity and before supply to the at least one blood analysis device, each at least one blood specimen can be associated with the identification code and the period of time code in the form of a barcode, a data matrix code and/or a transponder on an extraction device containing the at least one blood specimen.

4. The system according to claim 3 wherein the at least one blood analysis device comprises a read unit to read the barcode, the data matrix code and/or the transponder.

5. The system according to claim 4, wherein the at least one blood analysis device is connected with the calculation device which is connected with the supply devices for data transfers.

6. The system according to claim 3, wherein the extraction device is a syringe or a blood extraction tube, wherein a blood receiving container of the extraction device, or a blood receiving container connected to the extraction device, is connected with the barcode, the data matrix code and/or the transponder.

7. The system according to claim 1, wherein the data sets of the medicament parameters are encrypted.

8. The system according to claim 1, wherein within the common dataset, a data set of the medicament parameters with data of the identification code and the period of time code is frequency- and or amplitude-modulated.

9. The system according to claim 1, wherein the common data set is present in binary code.

10. A method for monitoring in each case at least one blood parameter of the blood of different patients, said method comprising the steps of:
  creating in each case, with a multiplicity of access devices, at least one access to the blood of each patient through his or her skin;
  extracting, with a multiplicity of extraction devices, a blood quantity from each patient to obtain in each case at least one blood specimen;
  analyzing, with at least one blood, analysis device, the blood specimen in relation to predefinable parameters of the blood;
  generating, with the at least one blood analysis device, individual blood parameter data sets;
  calculating, with a calculation device which can be used in common for a multiplicity of blood parameter data sets of the different patients, data sets of medicament parameters of medicaments to be administered to a respective patient on the basis of the individual blood parameter data sets;
  supplying, with a multiplicity of supply devices, the respective medicaments to the respective different patients in accordance with the calculated data sets of the medicament parameters for each of the different patients; and
  allocating in each case, with an association device, an identification code to identify a patient and a period of time code to specify a period of time in which the at least one blood specimen was taken, to each data set of the medicament parameters calculated by the calculation device, such that a common data set is created for each respective patient; and
  transmitting, with the association device, each common data set including a respective data set of the calculated data sets of the medicament parameters for each of the different patients from the calculation device, together with the identification code and the period of time code, by a hard-wired link or a wireless link to a respective supply device, wherein each respective supply device is selected based on the identification code and the period of time code; and
  supplying, with each respective supply device, a corresponding amount of a respective medicament according to the common data set for each respective patient.

* * * * *